United States Patent [19]

Riekkinen et al.

[11] Patent Number: 5,434,177
[45] Date of Patent: Jul. 18, 1995

[54] IMIDAZOLES FOR THE TREATMENT OF AGE-RELATED COGNITIVE DISORDERS AND ALZHEIMER

[75] Inventors: Paavo J. Riekkinen; Paavo Riekkinen, Jr.; Jouni S. I. Sirviö, all of Kuopio; Riitta A. Miettinen, Syvänniemi; Antti Valjakka, Kuopio; Mauno M. Airaksinen, Kuopio; Sakari A. Nieminen, Kuopio; Ewen MacDonald, Kuopio; Risto A. S. Lammintausta, Turku; Raimo E. Virtanen, Rusko, all of Finland

[73] Assignee: Orion-Yhtyma Oy, Espoo, Finland

[21] Appl. No.: 952,860

[22] PCT Filed: May 30, 1991

[86] PCT No.: PCT/FI91/00172
§ 371 Date: Nov. 30, 1992
§ 102(e) Date: Nov. 30, 1992

[87] PCT Pub. No.: WO91/18886
PCT Pub. Date: Dec. 12, 1991

[30] Foreign Application Priority Data

May 31, 1990 [GB] United Kingdom ............... 9012157

[51] Int. Cl.⁶ ........................................ A61K 31/415
[52] U.S. Cl. .................................... 514/399; 514/396; 514/400
[58] Field of Search .................... 514/396, 399, 400

[56] References Cited

U.S. PATENT DOCUMENTS 4,738,979 4/1988 Calderon et al. ............... 514/396
5,204,364 4/1993 Carganico et al. ............... 514/399

FOREIGN PATENT DOCUMENTS 0183492 6/1986 European Pat. Off.
0247764 12/1987 European Pat. Off.

OTHER PUBLICATIONS

CA: 115(23) 247997(a)–Servio et al (1991).
CA: 116(23) 228130s–Servio et al (1982).
CA: 117(1) 738 F–Servio et al (1992).
European Journal of Pharmacology, vol. 183, No. 3, 1990 Neiminen S. A. et al: "Effects of atipamezole, an alpha–2 antagonist, on memory retrieval in the rat", pp. 933–934.

Primary Examiner—Marianne M. Cintins
Assistant Examiner—T. J. Criares
Attorney, Agent, or Firm—Adduci, Mastriani, Schaumberg, Meeks & Schill

[57] ABSTRACT

This invention relates to the use of a compound of formula

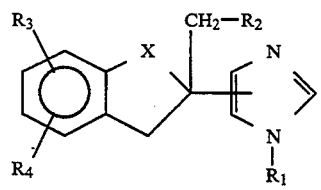

wherein X is —$CH_2$— or

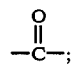

$R_1$ is H, $C_{1-5}$-alkyl or benzyl, which can be substituted of unsubstituted; $R_2$ is H, $C_{1-4}$-alkyl, $C_{1-4}$-alkenyl, OH, or $C_{1-3}$-alkoxy; $R_3$ is H, $CH_3$, $C_2CH_3$, $OCH_3$, or Hal; $R_4$ H, $CH_3$, $C_2CH_3$, $OCH_3$, or Hal, and Hal is halogen, provided that when $R_2$ is OH or $C_{1-3}$-alkoxy then X cannot be CO or a non-toxic pharmaceutically acceptable salt thereof for the use in the treatment of age related memory impairment or cognitive disorders, particularly Alzheimer's Disease.

4 Claims, No Drawings

IMIDAZOLES FOR THE TREATMENT OF AGE-RELATED COGNITIVE DISORDERS AND ALZHEIMER

This invention relates to the use of a group of certain $\alpha_2$-receptor antagonists for the treatment of age related memory impairment and other cognitive disorders, particularly Alzheimer's Disease.

The active compounds of the invention are imidazole derivatives which are potent and selective $\alpha_2$-receptor antagonists and have the general formula:

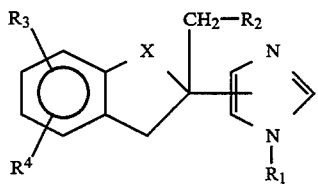

wherein
X is —CH$_2$— or

$R_1$ is H, $C_{1-5}$-alkyl or benzyl, which can be substituted or unsubstituted
$R_2$ is H, $C_{1-4}$-alkyl, $C_{1-4}$-alkenyl, OH or $C_{1-3}$-alkoxy
$R_3$ is H, CH$_3$, CH$_2$C$_3$, OCH$_3$ or Hal
$R_4$ is H, CH$_3$, CH$_2$C$_3$, OCH$_3$ or Hal, and Hal is halogen, such as F, Cl, Br or I,
provided that when $R_2$ is OH or $C_{1-3}$-alkoxy then X cannot be CO, and their non-toxic, pharmaceutically acceptable salts.

The compounds of the formula (I) form acid addition salts with both organic and inorganic acids. They can thus form many pharmaceutically usable acid addition salts, as for instance, chlorides, bromides, sulfates, nitrates, phosphates, sulfonates, formates, tartrates, maleates, citrates, benzoates, salicylates, ascorbates and the like.

Certain members of the above compounds have been earlier disclosed e.g. in EP 183492 and EP 247764 as selective $\alpha_2$-antagonists valuable as antagonists to veterinary sedatives and analgetics.

According to this invention compounds of formula (I) have been found to possess valuable pharmacological activities and they are thus believed to be useful in the treatment of age related memory impairment and their cognitive disorders.

Preferably $R_1$ is hydrogen, methyl or ethyl. If $R_1$ is benzyl it may optionally be substituted by one or more substituent chosen from $C_{1-4}$ alkyl, halogen and $C_{1-3}$ alkoxy. Preferably $R_2$ is H, methyl, ethyl, methoxy or ethoxy, most preferably methyl or methoxy.
$R_3$ and $R_4$ are preferably H.

Particularly valuable compounds of formula (I) are atipamezole or 4-(2-ethyl-2,3-dihydro-1H-inden-2-yl)-1H-imidazole, MPV-1260 BI or 1-methyl-4-(2-methoxymethyl-2,3-dihydro-1H-inden-2-yl)-1H-imidazole and MPV-1705 AI or 2-ethyl-2-(1-ethyl-1H-imidazole-4-yl)-1-indanone.

Anatomical and electrophysiological properties of noradrenergic neurons projecting from the locus coeruleus of the forebrain suggest that this system plays a role in selective attention, learning and memory. Dysfunction of the noradrenergic system, possibly in conjunction with dysfunction of the cholinergic system, may also underlie some aspects of age-related cognition deficits.

Impairment in cognitive functions, induced by pharmacological (e.g. scopolamine) or surgical manipulation (e.g. cholinergic nucleus basalis lesion) or age-related, have been shown to be associated with marked alterations in cortical EEG-recordings (increase in slow wave activity and number of high voltage spindles).

It has now been shown that the incidence of high voltage spindles is high in a sub-population of aged rats which shows impaired memory performance in the passive avoidance test. Compounds of this invention were able to markedly decrease the incidence of high voltage spindles in these animals. Pre-retention test injections of the compounds also improved passive avoidance performance.

Methods

Subjects:
Young adult (3 months) and aged (26 months) female Kuo:Wistar rats were used.

Passive avoidance
The passive avoidance apparatus consisted of a rectangular plexiglass box, divided into dark and lighted compartment by a sliding guillotine door. The dark compartment had a metal grid floor. Rats were placed in the lighted side. After 60 s a door opened into the dark side. 5 s after the entry to the dark side a 1.0 mA shock was delivered to the rat's feet. The shock remained on until the rat returned to the lighted side. Training continued until the rat remained on the lighted side for 60 s. Mean latency to first enter the dark chamber and number of re-entries were recorded during the training trial. Testing occured 6 days later. The rat was put on the lighted side and the door opened 60 s later. The session continued until the rat entered the dark side, or for 600 s. The latency to enter (retention latency) was recorded.

Neurophysiology
The animals were anesthetized with chloral hydrate (350 mg/kg) and placed in a stereotaxic frame with the incisor bar set at −3.3 mm. The active recording electrodes (stainless steel screws 0.5 mm in diameter) were located on the skull at the following coordinates: ML=3.0 mm, AP=2.0 and −7.0 mm relative to the bregma. The reference and ground electrodes were located in the midline above the cerebellum. The electrodes and connected female pins were embedded in dental acrylic. A recovery period of 7 days was allowed before any recording were taken.

The EEG values of rats were taken between 1000–1400 h. The rats were allowed to move freely in a plexiglass cage. Samples were obtained simultaneously from frontal and occipital recording sites. The incidence and duration of spike and wave HVSs (high voltage spindles, Aston-Jones & Bloom (1981a), Journal of Neuroscience, 1, 876–886) were analysed from polygraph charts using a ruler. The rats were recorded 15 minutes after saline or atipamezole (3 mg/kg s.c.) injections. In separate experiments MPV-1260 BI (30 mg/kg p.o.) and MPV-1705 AI (6 mg/kg p.o.) or NaCl were administered and EEG recordings were taken 1 and 4 hours later.

Results

Table 1 discloses the positive effect of atipamezole on the PA performance. Table 2 shows that atipamezole alleviates the EEG change (increase in the number of HVSs) induced by high age in rat. Table 3 shows that MPV-1260 BI and MPV-1705 AI have a similar effect.

TABLE 1

Retention of the inhibitory avoidance task.
Values are expressed as mean ± S.D.

| Group | Latency to enter |
|---|---|
| YC | 352 ± 91 |
| YA | 401 ± 33 |
| AC | 164 ± 231* |
| AA | 330 ± 78 |

*p < 0.05, Duncan's test.
Abbreviations:
YC = young controls (n = 10)
YA = young atipamezole 3 mg/kg (n = 10)
AC = aged controls (n = 10)
AA = aged atipamezole 3 mg/kg (n = 10)

TABLE 2

Effect of atipamezole on the number and duration (s) of high voltage spindles (HVS) in aged and young rats. Values are expressed as mean ± S.D.

|   | Number | Duration (s) |
|---|---|---|
| Y | 3 ± 3 | 4 ± 2 |
| A | 32 ± 34* | 4 ± 4 |
| AA | 4 ± 9● | 3 ± 6 |

*p < 0.05 vs young rats, Duncan's test
●p < 0.05 vs HVS values of aged rats recorded after saline injections, Wilcoxon signed ranks test.
Group abbreviations:
Y = young rats, saline injections
A = aged rats, saline injections
AA = aged rats, atipamezole 3 mg/kg injections

TABLE 3

The effect of α2-antagonists MPV-1260 BI and MPV-1705 AI on the number and duration of high voltage spindles in aged rats.

| Compound | Number | Duration (s) |
|---|---|---|
| Control (n = 4) | | |
| 1 h | 77 | 4.6 |
| 4 h | 88 | 5.7 |
| MPV-1260 BI 30 mg/kg (n = 4) | | |
| 1 h | 17 | 3.7 |
| 4 h | 63 | 6.2 |
| Mpv-1705 AI 6 mg/kg (n = 4) | | |
| 1 h | 5 | 3.4 |
| 4 h | 35 | 5.6 |

Pharmaceutical compositions for use in accordance with the present invention may be formulated in conventional manner using one or more physiologically acceptable carriers or excipients. The compounds of formula (I) and their physiologically acceptable salts are preferrably formulated for oral or parenteral administration. The pre#erable dose range is 0.1 to 1 mg/kg/day for parenteral administration and 1 to 10 mg/kg/day for oral administration.

We claim:

1. A method of treatment of memory impairment or other cognitive disorders comprising administering to a patient in need of such treatment an amount effective for treating memory impairment or other cognitive disorders of a compound of formula (I)

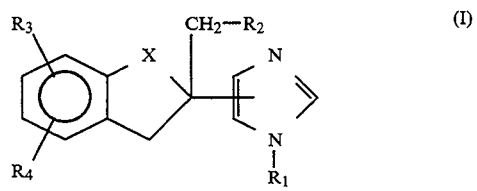

wherein
X is —$CH_2$— or

$R_1$ is H, $C_{1-5}$-alkyl or benzyl, which can be substituted or unsubstituted,
$R_2$ is H, $C_{1-4}$-alkyl, $C_{1-4}$-alkenyl, OH or $C_{1-3}$-alkoxy,
$R_3$ is H, $CH_3$, $CH_2CH_3$, $OCH_3$ or Hal,
$R_4$ is H, $CH_3$, $CH_2CH_3$, $OCH_3$ or Hal, and Hal is halogen, provided that when $R_2$ is OH or $C_{1-4}$-alkoxy then X cannot be CO, or a non-toxic pharmaceutically acceptable salt thereof.

2. The method according to claim 1 where the compound of formula (I) is atipamezole or its non-toxic, pharmaceutically acceptable acid addition salt.

3. The method according to claim 1 where the compound of formula (I) is 1-methyl-4-(2-methoxymethyl-2,3-dihydro-1H- inden-2yl)-1H-imidazole or its non-toxic, pharmaceutically acceptable acid addition salt.

4. The method according to claim 1 where the compound of formula (I) is 2-ethyl-2(1-ethyl-1H-imidazol-4-yl)-1-indanone or its non-toxic, pharmaceutically acceptable acid addition salt.

* * * * *